(12) United States Patent
Kudoh

(10) Patent No.: US 10,413,670 B2
(45) Date of Patent: Sep. 17, 2019

(54) NEEDLELESS SYRINGE

(75) Inventor: Masatake Kudoh, Myoko (JP)

(73) Assignee: Daicel Corporation, Osaka (JP)

( * ) Notice: Subject to any disclaimer, the term of this patent is extended or adjusted under 35 U.S.C. 154(b) by 1353 days.

(21) Appl. No.: 14/344,581

(22) PCT Filed: Sep. 12, 2012

(86) PCT No.: PCT/JP2012/073377
§ 371 (c)(1),
(2), (4) Date: Oct. 9, 2014

(87) PCT Pub. No.: WO2013/039121
PCT Pub. Date: Mar. 21, 2013

(65) Prior Publication Data
US 2015/0032082 A1 Jan. 29, 2015

(30) Foreign Application Priority Data

Sep. 12, 2011 (JP) ................... 2011-198899

(51) Int. Cl.
*A61M 5/30* (2006.01)
*A61M 5/20* (2006.01)
*A61M 5/31* (2006.01)

(52) U.S. Cl.
CPC ............ *A61M 5/30* (2013.01); *A61M 5/2046* (2013.01); *A61M 5/3007* (2013.01); *A61M 2005/3132* (2013.01)

(58) Field of Classification Search
CPC .... A61M 5/30; A61M 5/3007; A61M 5/2046; A61M 2005/3132
See application file for complete search history.

(56) References Cited

U.S. PATENT DOCUMENTS 6,503,231 B1    1/2003  Prausnitz et al.
6,623,446 B1 *  9/2003  Navelier ................ A61M 5/30
                                                         604/68

(Continued)

FOREIGN PATENT DOCUMENTS

JP    2000-014780 A    1/2000
JP    2003-504161      2/2003

(Continued)

OTHER PUBLICATIONS

Office Action dated Feb. 13, 2018 in related Japanese Application No. 2017-067331.

(Continued)

*Primary Examiner* — Imani N Hayman
*Assistant Examiner* — Tiffany Legette
(74) *Attorney, Agent, or Firm* — Knobbe Martens Olson & Bear LLP

(57) ABSTRACT

A needleless syringe comprises an enclosing unit for an injection objective substance, a pressurizing unit for the injection objective substance, a discharge unit having a flow passage for allowing the injection objective substance to flow therethrough so that the injection objective substance is discharged from an open end of the flow passage to an injection target area, the open end being formed so that an area thereof is smaller than a flow passage area of the enclosing unit, and a minute pore unit including a minute pore having a flow passage area smaller than the area of the open end of the discharge unit and which is arranged on an outer side of the open end so that the injection objective substance discharged from the open end passes through the minute pore and arrives at a side of the injection target area.

14 Claims, 12 Drawing Sheets

(56) References Cited

U.S. PATENT DOCUMENTS

| | | | |
|---|---|---|---|
| 6,716,190 B1* | 4/2004 | Glines | A61M 5/3007 604/141 |
| 2004/0210188 A1 | 10/2004 | Glines et al. | |
| 2006/0281175 A1 | 12/2006 | McSwiggen et al. | |
| 2007/0055214 A1* | 3/2007 | Gilbert | A61M 5/30 604/500 |
| 2008/0132450 A1 | 6/2008 | Lee et al. | |
| 2010/0076375 A1 | 3/2010 | Alexandre | |

FOREIGN PATENT DOCUMENTS

| | | |
|---|---|---|
| JP | 2005-523679 A | 8/2005 |
| JP | 2007-518460 A | 7/2007 |
| JP | 2007-525192 A | 9/2007 |
| JP | 2008-508881 A | 3/2008 |
| JP | 2008-206477 A | 9/2008 |
| JP | 2010-503504 A | 2/2010 |
| JP | 2010-503616 A | 2/2010 |
| WO | WO 03/004620 A2 | 1/2003 |
| WO | WO 2004/101025 A2 | 11/2004 |
| WO | WO 2006/015373 A2 | 2/2006 |

OTHER PUBLICATIONS

International Preliminary Report on Patentability in International Application No. PCT/JP2012/073377 dated Oct. 30, 2012.
Office Action issued in corresponding Japanese Application 2015-189674 dated Aug. 16, 2016.
Final Decision of Rejection dated Sep. 4, 2018 in related Japanese Application No. 2017-067331.

* cited by examiner

NEEDLELESS SYRINGE

CROSS-REFERENCE TO RELATED APPLICATIONS

This application claims priority to Japanese Patent Application No. 2011-198899 filed on Sep. 12, 2011, the entire contents of which are incorporated by reference herein.

TECHNICAL FIELD

The present invention relates to a needleless syringe with which an injection objective substance is injected into an injection target area of a living body without using an injection needle.

BACKGROUND ART

In the case of a needleless syringe with which the injection is performed without using an injection needle, such a construction is adopted that an injection component is discharged by applying the pressure to an injection solution containing a medicament or the like by means of a pressurized gas or a spring. The pressurizing force, which is applied to the injection solution, is adjusted so that the injection solution can be delivered to an intended area in the living body. In this context, the ability, which makes it possible to administer the medicament to Langerhans cells in the skin, is especially remarked when the medicament is injected into the living body by using, for example, the needleless syringe. Langerhans cells are dendritic cells ordinarily existing in the upper stratum spinosum of the skin. It is known that the cells relate to the immune response of the skin, and the cells migrate from the skin to the lymph node. The cells have the common receptor for macrophage, and the cells function as the antigen-presenting cells for T lymphocyte and B lymphocyte. Therefore, Langerhans cells are especially important in the acceleration of vaccine development and the research on the immune system relevant to the treatment to prevent and cure the autoimmune disease and the rejection symptom. However, Langerhans cells exist at a relatively shallow region of the skin. Therefore, the efficient execution of the administration of the injection solution to Langerhans cells is extremely effective for the needleless syringe which does not have any injection needle for directly carrying the injection solution to the inside of the living body.

On the other hand, Patent Document 1 discloses such a technique that the shallow intradermal injection into the region in which Langerhans cells exist can be achieved. According to the technique, the interior of a syringe is allowed to be in a vacuum state by means of suction generating means to form a state in which the skin tissue is pressed against an orifice from which the injection solution is discharged. The injection solution is discharged with a jet flow having a velocity sufficient to cause the permeation into the pressed skin tissue.

CITATION LIST

Patent Document

Patent Document 1: JP2007-518460A.

SUMMARY OF INVENTION

Technical Problem

Since the needleless syringe has no injection needle, it has a preferred structure in a hygienic viewpoint as well and thus it is expected to be used in the broad field. On the other hand, because there is no injection needle, it is necessary to perform the control in order to carry the injection solution to an intended area. If it is intended that the interior of the syringe is formed to be in the vacuum state so that the skin of the living body is pressed against the discharge port for the injection solution as in the conventional technique, the structure of the syringe itself becomes stout and complex in order to maintain the preferred vacuum state. Further, any auxiliary machine such as a pump or the like is required to form the vacuum state. It is not preferable that the convenience as the syringe may be extremely diminished.

Taking the foregoing problem into consideration, an object of the present invention is to provide a needleless syringe which makes it possible to perform the injection into a relatively shallow region of an injection target area of a living body or the like and which has a structure that is simplified to a maximum extent.

Solution to Problem

In order to achieve the object as described above, in the present invention, attention is focused on the flow diameter of an injection objective substance (for example, an injection solution) at the time of discharge from a needleless syringe to the outside of the syringe. Specifically, the flow diameter is the diameter of the liquid column provided when the injection objective substance passes through a nozzle or the like and is discharged to the outside of the syringe and it is the diameter of the flow of the discharged injection objective substance that is considered as one of the great factors to determine the depth at which the injection objective substance arrives in the injection target area of a living body. The smaller the flow diameter is, the easier it becomes to conduct the control to keep the depth of the penetration of the injection objective substance shallow.

Specifically, the present invention resides in a needleless syringe for injecting an injection objective substance into an injection target area of a living body without using an injection needle; the needleless syringe comprising an enclosing unit which encloses the injection objective substance; a pressurizing unit which pressurizes the injection objective substance enclosed in the enclosing unit; a discharge unit which has a flow passage for allowing the injection objective substance pressurized by the pressurizing unit to flow therethrough so that the injection objective substance is discharged from an open end of the flow passage to the injection target area outside the syringe, the open end being formed so that an area thereof is smaller than a flow passage area of the enclosing unit; and a minute pore unit which includes a minute pore having a flow passage area smaller than the area of the open end of the discharge unit and which is arranged on an outer side of the open end so that the injection objective substance discharged from the open end passes through the minute pore and arrives at a side of the injection target area.

In the needleless syringe according to the present invention, the pressure is applied by the pressurizing unit to the injection objective substance enclosed in the enclosing unit, and thus the movement of the injection objective substance from the flow passage of the enclosing unit to the flow passage of the discharge unit is facilitated. As a result, the injection objective substance is discharged from the open end of the discharge unit to the injection target area. The injection objective substance contains the component for which the efficacy is expected at the inside of the injection target area. The pressure, which is applied by the pressurizing unit as described above, is the driving force when the injection objective substance is discharged. Therefore, on condition that the discharge can be performed by the pressurizing unit, particular states of containment of the injection objective substance in the needleless syringe or specific physical forms of the injection objective substance, such as liquid, gel-like fluid, powder, granular material, etc., are not required.

For example, the injection objective substance may be a liquid. Even if the injection objective substance is a solid, it may be a gel-like solid as long as the fluidity that enables the injection objective substance to be discharged is ensured. Further, the injection objective substance may be in a powdery state. In the injection objective substance, those components that are to be delivered to the injection target area of the living body are contained. The components may exist in a state of being dissolved in the injection objective substance or in a state in which the component is not dissolved but is only mixed. By way of example, the components to be delivered may be vaccines to enhance the antibody, proteins for cosmetic purposes, cultured cells for hair regeneration. The injection objective substance is formed by the components as described above being contained in the fluid such as liquid, gel or the like so that the components can be discharged.

As for the pressurizing source to pressurize the injection objective substance, it is possible to utilize various pressurizing sources provided that the discharge can be performed by means of the pressurization. Those exemplified as the pressurizing source include, for example, those that utilize the elastic force generated by the spring or the like, those that utilize the pressurized gas, those that utilize the pressure of the gas produced by the combustion of the propellant and those that utilize the electric actuator for the pressurization (a motor, a piezoelectric element, or the like). It is also possible to adopt a form in which the pressurization is achieved by hand motions of the user.

The area of the open end of the discharge unit is formed to be smaller than the flow passage area of the enclosing unit. The area referred to herein is the area provided in the direction perpendicular to the flow of the injection objective substance. When the area of the open end is set as described above, the pressurized injection objective substance is converged at the open end having the smaller flow passage area, and it is possible to raise the pressure applied to the injection objective substance upon discharge. Accordingly, the discharged injection objective substance can penetrate through the surface of the injection target area of the living body, and the discharged injection objective substance can permeate the inside thereof.

In the needleless syringe according to the present invention, the minute pore unit is arranged at the outside of the open end. That is, the minute pore of the minute pore unit is a "pore" which is provided as a different structure from the open end of the discharge unit. The minute pore has the flow passage area smaller than the area of the open end. The injection objective substance, which is discharged from the open end of the discharge unit, passes through the minute pore of the minute pore unit before the injection objective substance arrives at the injection target area. As a result, the flow diameter of the injection objective substance that passed through the minute pore is smaller than the flow diameter provided when the injection objective substance is discharged from the open end, depending on the flow passage area of the minute pore. A plurality of minute pores may be formed. In this case, in other words, one flow discharged from the open end is divided into a plurality of thin flows so that the flow diameter is reduced by means of the minute pore unit. Therefore, the flows of the injection objective substance having the small flow diameter arrive at the surface of the injection target area. Thus, it is possible to adjust the depth to be shallow in the injection target area at which the injection objective substance arrives.

When the injection objective substance can be injected into the shallow region by adopting the simple construction in which the minute pore unit is arranged outside the open end of the discharge unit as described above, then the needleless syringe can be supplied at a low cost and it is also possible to avoid the diminishment of the convenience of users. Further, the injection objective substance can be injected into an intended region. Therefore, it is possible to realize the efficient injection of the injection objective substance, that is, it is possible to suppress the consumption of wasted injection objective substance upon injection. When the flow passage area of the minute pore unit is appropriately selected, it is possible to easily control the injection depth in the injection target area even when the pressurization, which is exerted on the injection objective substance by the pressurizing unit, is not adjusted.

The minute pore unit is formed as the different structure from the discharge unit having the open end, and the minute pore unit is arranged outside the open end of the discharge unit. Therefore, it is not necessarily needed that the minute pore unit should be formed integrally with the discharge unit in the needleless syringe. The minute pore unit and the discharge unit may be formed as separate members. Therefore, when the minute pore unit and the discharge unit are formed as separate members, then each unit can be formed with different materials, and each unit can be produced by different production methods as well. In particular, the minute pore unit has the minute pore having the smaller flow passage area. Therefore, when the material and the production method, which are different from those for the open end of the discharge unit, are adopted, it is also possible to easily produce the needleless syringe. The number of the minute pores is not limited.

The needleless syringe described above may be constructed to have a minute pore planar member which is formed with a plurality of the minute pores and which is arranged with the minute pores in a planar form; and an attachment member which is attached to a side of the discharge unit in a state of holding the minute pore planar member and which is arranged in an attached state thereof so that the minute pore planar member covers the open end of the discharge unit. When the construction as described above is adopted, then the attachment to the side of the discharge unit is performed by the attachment member, and the minute pore planar member is held by the attachment member. Accordingly, it is possible to easily perform the relative arrangement of the minute pore with respect to the open end of the discharge unit. By making the attachment to the discharge unit by the attachment member detachable, the minute pore unit can be appropriately exchanged in view of required injection depth in the injection target area or hygienic aspect. When exchanging the minute pore unit as described above, the entire minute pore unit may be exchanged or the minute pore planar member may be exchanged with respect to the attachment member detached from the discharge unit. In particular, forming the open end with a small diameter in the discharge unit involves processing difficulties. However, in the present invention, it is possible to use a porous plate member having a predetermined opening area (for example, lath metal, punching metal and mesh sheet) or the like as the minute pore planar member, and thus the minute pore unit can be formed with ease.

The needleless syringe described above may be constructed such that the minute pore planar member is brought into contact with the open end of the discharge unit in the attached state of the attachment member to the side of the discharge unit, and the pressurized injection objective substance flows into the minute pores from the open end. The minute pore planar member is arranged to be brought into contact with the open end, and thus the open end is covered with the minute pore planar member. As a result, the injection objective substance, which is discharged from the open end, is divided by the minute pore planar member and an efficient injection into the relatively shallow region in the injection target area is realized. Further, it is possible to suppress the injection solution to be remained between the minute pore planar member and the discharge unit, and thus it is possible to eliminate a wasteful consumption of the injection objective substance.

In the needleless syringe as described above, when in a state in which the minute pore planar member is held by the attachment member, an outer surface of the minute pore planar member may be flush with an outer surface of the attachment member to be brought into contact with the injection target area at the time of injection. By making the outer surface of the minute pore planar member flush with the outer surface of the attachment member, when the discharge unit of the needleless syringe is brought into contact with the injection target area at the time of injection to the area, the formation of any unnecessary gap between the minute pore planar member and the area within the range in which the injection objective substance is discharged can be avoided. If the gap exists, a part of the discharged injection objective substance may remain on the surface of the injection target area, and hence the substance may be wasted. In view of the above, in order to realize a precise injection, it is preferable that the gap is eliminated as much as possible. Therefore, it is favorable, especially in terms of efficiently realizing a injection into the relatively shallow region in the injection target area, to adopt the construction in which the surfaces are flush with each other as described above. In particular, when the injection target area is a substantially planar region to such an extent that the attachment member makes contact with the injection target area, it is preferable that the surfaces are flush with each other as described above.

In the needleless syringe as described above, the minute pore planar member may be attached to and detached from the attachment member such that the minute pore planar member is exchangeable with another minute pore planar member. That is, by exchanging the minute pore planar member of the minute pore unit, the control of the injection depth and the securement of the preferred hygienic condition in response to the type and the region of the injection target area can be realized.

Further, in the needleless syringe as described above, the attachment member may be fixed to the discharge unit by being press-fitted into the discharge unit. By attaching the attachment member by press-fitting, the minute pore unit can be disposed more firmly with respect to the open end of the discharge unit. As for the modes of attaching the attachment member, a snap-fit that employs an engaging technique, a screw-fit that employs a screwing technique, a tightening by elastic members or the like can be applied.

The present invention can also be considered in an aspect of an operation method for operating a needleless syringe. That is, the present invention resides in an operating method for operating a needleless syringe for injecting an injection objective substance into an injection target area without using an injection needle, the needleless syringe comprising an enclosing unit which encloses an injection objective substance, and a pressurizing unit which pressurizes the injection objective substance enclosed in the enclosing unit. And the operating method comprises a step of pressurizing the injection objective substance enclosed in the enclosing unit by the pressurizing unit; a step of allowing the injection objective substance pressurized by the pressurizing unit to flow into a flow passage in an discharge unit, the flow passage having an open end for discharging the injection objective substance to an injection target area outside the syringe, an area of the open end being formed to be smaller than a flow passage area of the enclosing unit; and a step of allowing the injection objective substance to pass through a minute pore unit including a minute pore arranged on an outer side of the open end and having a flow passage area smaller than an area of the open end of the discharge unit, before the injection objective substance, which is discharged from the open end, arrives at the injection target area. When the needleless syringe is operated as described above, it is possible to efficiently perform the injection into the relatively shallow region of the injection target area of the living body or the like as described above.

In the operating method for operating the needleless syringe as described above, it is also preferable that the minute pore unit is formed by a minute pore planar member which is formed with a plurality of minute pores in a planar form, and an attachment member which holds the minute pore planar member on a side of the discharge unit and which is attached to the discharge unit; and the minute pore planar member is attached by the attachment member so that the minute pore planar member is brought into contact with the open end of the discharge unit. Further, the construction is made such that the injection objective substance is allowed to flow into the minute pores of the minute pore planar member when the injection objective substance passes through the minute pore unit in the step of allowing the injection objective substance to pass through. Accordingly, the injection objective substance can be supplied to a wide range of the injection target area in a surface direction. It is noted that the surface direction is the direction which is not the injection depth direction in which the injection is performed, and the surface referred to in the surface direction resides in a concept which includes not only the flat surface but also the curved surface such as the spherical surface or the like.

Further, the technical idea in relation to the needleless syringe according to the present invention disclosed above is also applicable to the invention concerning the operation method for operating the needleless syringe.

Further, in this context, the present invention can also be considered in an aspect of a method for using the needleless syringe. That is, the present invention resides in a method for using a needleless syringe comprising an enclosing unit which encloses an injection objective substance; a pressurizing unit which pressurizes the injection objective substance enclosed in the enclosing unit; and a discharge unit which includes a flow passage having an open end for discharging the injection objective substance to an injection target area outside the syringe, the open end being formed to have an area smaller than a flow passage area of the enclosing unit so that the injection objective substance is injected into the injection target area without using any injection needle. The method for using the needleless syringe comprises a step of disposing, on an outer side of the open end, a minute pore unit including a minute pore having a flow passage area smaller than an area of the open end; a step of pressurizing the injection objective substance enclosed in the enclosing unit by the pressurizing unit; a step of allowing the injection objective substance pressurized by the pressurizing unit to flow into the discharge unit; and a step of allowing the injection objective substance to pass through the minute pore unit before the injection objective substance is discharged from the open end and arrives at the injection target area. When the needleless syringe is used as described above, it is possible to efficiently perform the injection into the relatively shallow region of the injection target area of the living body or the like as described above. Further, the technical idea in relation to the needleless syringe according to the present invention disclosed above is also applicable to the invention concerning the method for using the needleless syringe.

Advantageous Effects of Invention

A needleless syringe which can perform an injection into a relatively shallow region of an injection target area of a living body or the like and has a structure that is simplified to a maximum extent can be provided.

DESCRIPTION OF EMBODIMENTS

A needleless syringe 1 (hereinafter simply referred to as "syringe 1") according to an embodiment of the present invention will be explained below with reference to the drawings. The construction of the following embodiment is described by way of example, and the present invention is not limited to the construction of the embodiment.

Figure 1A:
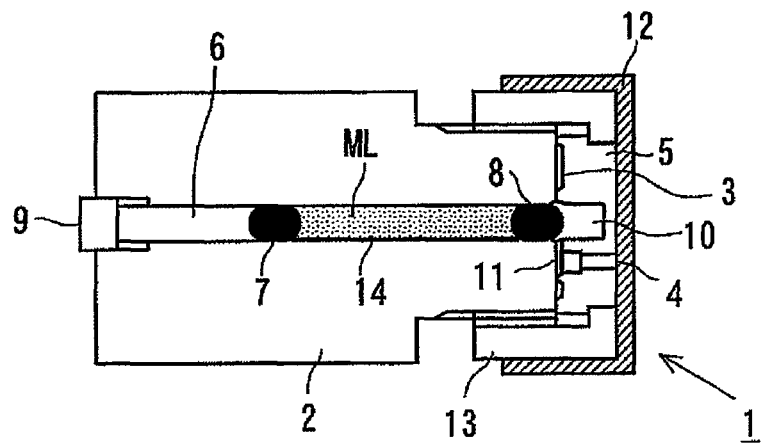
FIGS. 1A and 1B show a schematic construction of a needleless syringe according to the present invention.
Figure 1B:
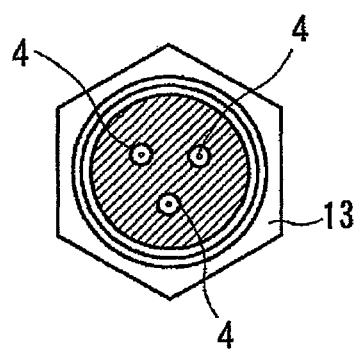

In this description, FIG. 1A shows a sectional view illustrating the syringe 1, and FIG. 1B shows a side view illustrating the syringe 1 as viewed from the side of a nozzle 4 for discharging an injection solution. In the following description of this application, an injection objective substance, which is injected into an injection target by the syringe 1, is generally referred to as "injection solution". However, this involves no intention to limit the contents and the form of the substance to be injected. As for the injection objective substance, it is also allowable that a component, which is to be delivered to the skin structure, is either dissolved or not dissolved. On condition that the injection objective substance can be discharged from the nozzle 4 to the skin structure by being pressurized, specific forms of the injection objective substance are not required and thus various forms including liquid form, gel-like form or the like can be adopted.

The syringe 1 has a main syringe body 2. A through-hole 14, which extends in the axial direction and which has a constant diameter in the axial direction, is provided at the central portion of the main syringe body 2. A piston 6 made of metal is arranged in the through-hole 14 so that the piston 6 is slidable in the axial direction in the through-hole 14. One end of the piston 6 is exposed to the side of a pressurizing unit 9, and a sealing member 7 is integrally attached to the other end of the piston 6. The injection solution ML, which is the injection objective substance to be injected by the syringe 1, is accommodated in the space formed in the through-hole 14 between the sealing member 7 and another sealing member 8. Therefore, the enclosing unit of the needleless syringe according to the present invention is formed by the sealing members 7, 8 and the through-hole 14. The sealing members 7, 8 are made of rubber having surfaces thinly applied with silicon oil so that the injection solution does not leak when the injection solution ML is enclosed, and the injection solution ML can be smoothly moved in the through-hole 14 in accordance with the sliding movement of the piston 6.

The pressurizing unit 9 serves as the source of driving force for the injection in the syringe 1. The pressure, which is generated by the pressurizing unit 9, is transmitted to the injection solution ML via the piston 6 and the sealing member 7. Accordingly, the discharge of the injection solution ML is started. In this arrangement, the pressurization, which is performed by the pressurizing unit 9, is based on the form which utilizes the elastic force of a spring. For example, the following construction is exemplified. That is, when a user presses a portion protruding from the main syringe body 2 at one end of the pressurizing unit 9 shown in FIG. 1A, the spring, which has been compressed in the pressurizing unit 9, is released, and then the elastic force, which is generated thereby, is transmitted to the piston 6. The pressurizing construction, which utilizes the elastic force of the spring, is based on the conventional technique as described, for example, in JP2000-14780A. It is possible to adopt various modified embodiments, for example, with the objective of appropriately adjusting the pressurizing force with respect to the purpose of the injection or from the standpoint of user convenience.

A holder 5, on which the nozzle 4 for discharging the injection solution ML is mounted, is provided on the forward end side of the syringe 1 (right side as shown in FIG. 1A). In the syringe 1, the nozzle 4 is of the so-called disposable type. In this construction, the nozzle 4 is detachably held in the holder 5 so that the nozzle 4 can be replaced with a new nozzle every time when the injection solution ML is discharged. The holder 5 is fixed to the end surface of the main syringe body 2 with the aid of a holder cap 13 with a gasket 3 intervening therebetween. The holder cap 13 is formed to have a brim-shaped cross section so that the holder cap 13 hooks on the holder 5, and the holder cap 13 is screw-fixed to the main syringe body 2. Accordingly, the holder 5 is prevented from falling off from the main syringe body 2 by the pressure applied to the injection solution ML during the discharge of the injection solution ML. In the example shown in FIG. 1A, the outer surface of the holder 5 is generally flush with the outer surface of the holder cap 13 in the attached state of the holder 5.

A recess 10 is formed, at a portion opposed to the sealing member 8 in the holder 5 such that the sealing member 8 can be accommodated therein, in the state in which the holder 5 is attached to the main syringe body 2 (state shown in FIG. 1A). The recess 10 has substantially the same diameter as that of the sealing member 8, and the recess 10 has the length slightly longer than the length of the sealing member 8. Accordingly, when the pressure is applied to the piston 6 and the injection solution ML is moved to the forward end side of the syringe 1 together with the sealing members 7, 8, then the sealing member 8 can be accommodated in the recess 10. When the sealing member 8 is accommodated in the recess 10, the pressurized injection solution ML is released from the enclosed state. Accordingly, a flow passage 11 is formed at a portion of the holder 5 to be brought into contact with the side of the main syringe body 2 so that the released injection solution ML is guided to the nozzle 4. The flow passage diameter of the interior of the nozzle 4 is smaller than the flow passage diameters of the through-hole 14 and the flow passage 11 as well. Accordingly, the released injection solution ML passes through the flow passage 11 and flows into the nozzle 4, and the flow having a relatively small flow diameter is formed therein. The flow is discharged to the skin of the living body as the injection target. Further, the recess 10 has the depth to accommodate the sealing member 8, and thus it is possible to avoid the discharge of the injection solution ML from being disturbed by the sealing member 8.

A plurality of nozzles 4 may be formed on the holder 5, or one nozzle 4 may be formed thereon. When a plurality of nozzles are formed, the flow passages corresponding to the respective nozzles are formed so that the released injection solution is delivered into the respective nozzles. When the plurality of nozzles 4 are formed, as shown in FIG. 1B, it is preferable that the nozzles are arranged at equal intervals around the central axis of the syringe 1. In this embodiment, three nozzles 4 are arranged in the holder 5 at equal intervals around the central axis of the syringe 1. The diameter of the nozzle 4 (diameter of the open end) is appropriately set in consideration of, for example, the injection target, the output pressure applied to the injection solution ML, the physical property (viscosity) of the injection solution, and the injection depth into the injection target. However, the nozzle 4 is produced by using a resin material by utilizing, for example, the injection molding. Therefore, as for the diameter thereof, the nozzle 4 has a diameter of submillimeter order even when the diameter is small.

In the syringe 1 constructed as described above, a masking member 12 is attached to the holder 5 fixed by the holder cap 13 so that the open end of the nozzle 4, i.e. the opening portion for discharging the pressurized injection solution to the outside, is covered therewith. The masking member 12 is provided with a mesh sheet member having minute pores as described later on. The injection solution ML, which is discharged from the open end of the nozzle 4, passes through the mesh sheet member, and the injection solution ML is discharged to the skin of the living body. The pressure is applied to the discharged injection solution ML. Therefore, the injection solution penetrates through the skin surface of the living body, and the injection solution arrives at the inside thereof. Thus, it is possible to achieve the object of the injection with the syringe 1.

Figure 2:
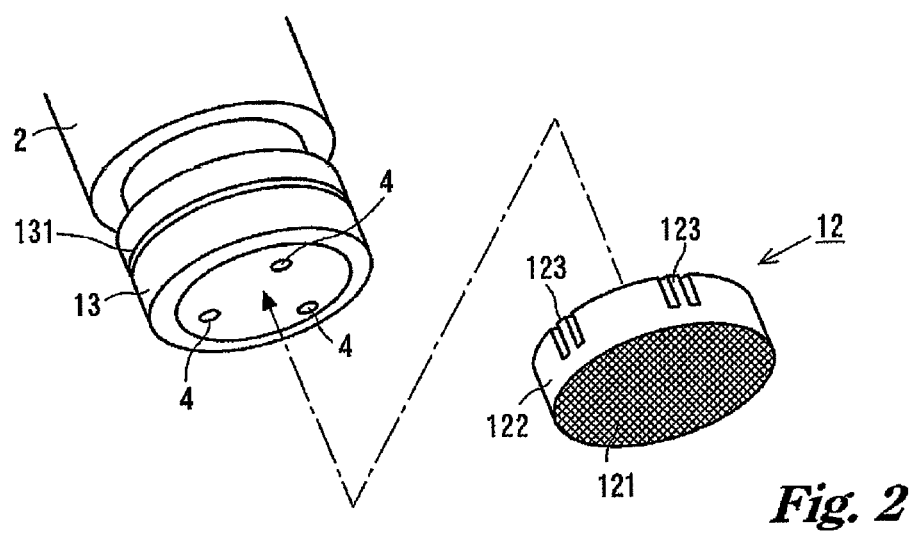
FIG. 2 shows a situation in which a masking member is being mounted on the needleless syringe shown in FIG. 1A.
Figure 3:
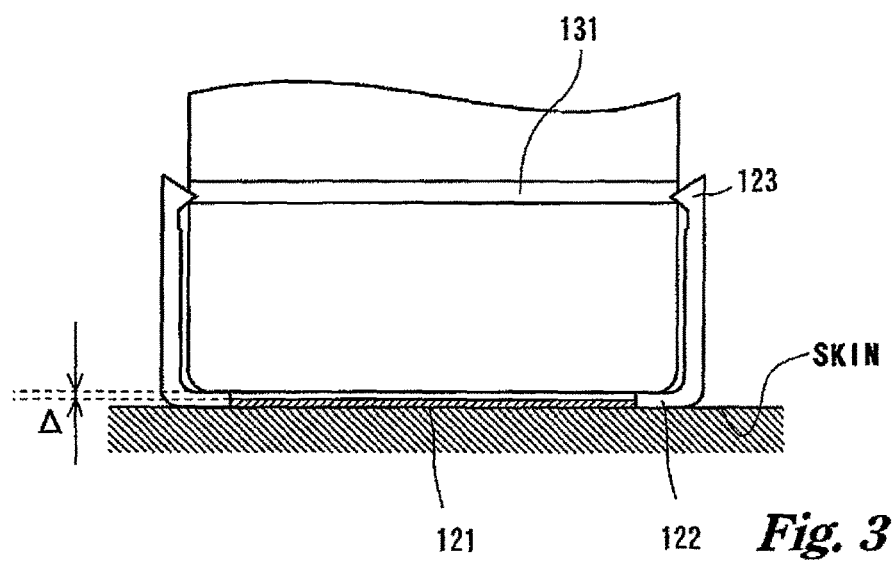
FIG. 3 shows a sectional view illustrating a state in which the masking member is mounted on the needleless syringe shown in FIG. 1A.
Figure 4:
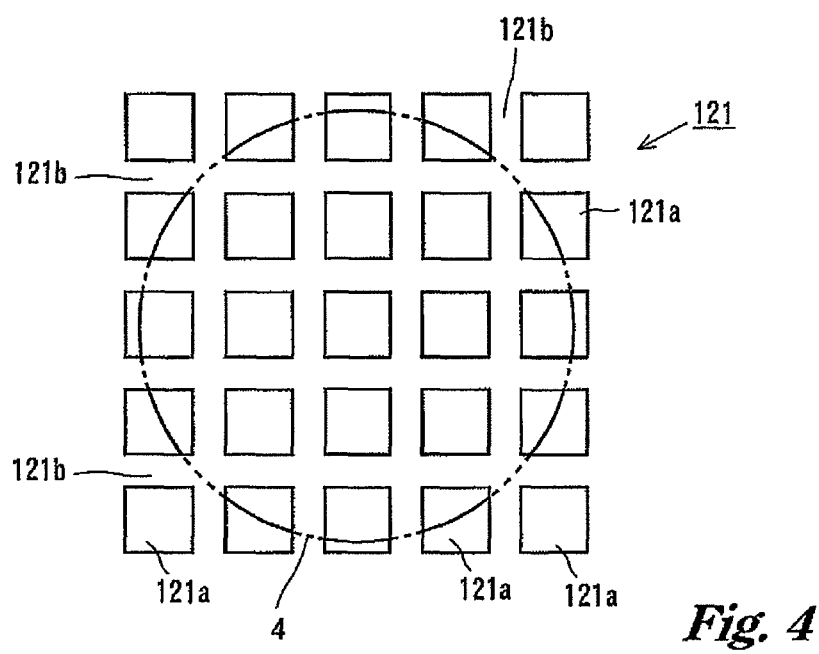
FIG. 4 shows an open end of a nozzle and minute pores depicted in an overlapped manner in the state in which the masking member is mounted on the needleless syringe shown in FIG. 1A.

An explanation will now be made in detail on the basis of FIGS. 2 to 4 about the discharge of the injection solution with the syringe 1 according to the embodiment of the present invention. FIG. 2 shows the construction of the side of main syringe body 2 and the masking member 12 attached to cover the open end of the nozzle 4 as described above. FIG. 3 shows a sectional view illustrating the state in which the masking member 12 is attached to the side of the main syringe body 2. FIG. 4 shows the open end of the nozzle 4 on the side of the main syringe body 2 and the minute pores provided on the side of the masking member 12 while overlapping the both so that the sizes of the both can be compared with each other. The masking member 12 has the mesh sheet member 121 which has the minute pores arranged substantially regularly, and an attachment cap 122 which is provided for the mesh sheet member 121 to be fixed and held. Chemical fiber fabric for medical use (for example, MEDIFAB produced by SEFAR and Falcon cell strainer produced by BD (Becton, Dickinson and Company)) can be utilized as the mesh sheet member 121. In the mesh sheet member 121, as shown in FIG. 4, the chemical fiber composed of polyamide, polyester or the like is arranged in a lattice form to form a lattice portion 121b. A state, in which the minute pores 121a are arranged regularly, is formed by the lattice portion 121b surrounding the four sides of each of the minute pores 121a. The minute pores 121a are substantially square-shaped. One side thereof can be appropriately selected depending on the way of use. One side has a size of, for example, 40 μm to 100 μm. In the form shown in FIG. 4, the minute pores 121a having the size and the shape as described above are regularly arranged on a plane at intervals of 100 μm to 150 μm.

In this construction, the diameter of the open end of the nozzle 4 is of the submillimeter order as described above, and the diameter is, for example, 0.2 mm. In such a case, as shown in FIG. 4, the area per one minute pore 121a of the mesh sheet member 121 is smaller than the area of the open end of the nozzle 4. Such a correlation of size is given that about several pieces of the minute pores 121a of the mesh sheet member 121 are included in one open end of the nozzle 4. The mesh sheet member 121 as described above is fixed to the attachment cap 122, and pawls 123, which are possessed by the attachment cap 122, are engaged with a groove 131 provided on the side surface of the holder cap 13. Thus, the masking member 12 is attached to the side of the main syringe body 2 (see FIG. 3). When the attachment is performed as described above, and thus the pressurization is performed by the pressurizing unit 9, then the injection solution ML passes through the open end of the nozzle 4 and the mesh sheet member 121, and the injection solution ML is discharged to the skin of the living body.

When the injection solution ML flows out from the open end of the nozzle 4, the injection solution is the flow having a flow diameter in accordance with the size of the open end. However, the injection solution ML arrives at the mesh sheet member 121 just thereafter, and thus the injection solution ML passes through the plurality of minute pores 121a provided in the mesh sheet member 121. As a result, the flow of the injection solution ML is thinly divided in accordance with the minute pores 121a arranged in the mesh sheet member 121. In other words, the flow of the injection solution ML, which flows from the open end of the nozzle 4, is divided into a plurality of flows each having a smaller flow diameter by the minute pores 121a. The plurality of divided flows finally arrive at the skin as the injection solution from the syringe 1.

As for the flow of the injection solution discharged from the syringe 1, provided that the flow rate of the injection solution is the same, the smaller the flow diameter becomes, the smaller the distance that the injection solution advances in the skin, i.e. the injection depth, becomes. Therefore, the injection depth in the skin as the injection target for the injection solution ML that is thinly divided by the mesh sheet member 121 becomes shallower than that in a situation where the injection solution ML is not thinly divided. Therefore, the syringe 1 shown in FIGS. 1 to 4 makes it possible to effectively deliver the injection solution to the relatively shallow region of the skin. On account of the existence of the mesh sheet member 121, the resistance acts against the flow of the injection solution, and the flow rate of the injection solution may be lowered. However, sufficient kinetic energy for the penetration through the skin surface and the advancement in the skin may be given by applying the adequate pressure to the injection solution ML by adjusting the pressurizing force exerted by the pressurizing unit 9 (i.e. the elastic force of the spring). As for the injection depth, the size of the minute pore 121*a* of the mesh sheet member is appropriately selected, and thus it is possible to effectively realize the injection especially into the shallow region of the skin at which Langerhans cells exist.

The minute pore 121*a* of the mesh sheet member 121 shown in FIG. 4 approximately has the square shape. However, it is also allowable to adopt minute pores having any shape other than the square, on condition that the area of the minute pore is smaller than the area of the open end of the nozzle 4, preferably on condition that the area of the minute pore is small to such an extent that several pieces of the minute pores are included in the open end of the nozzle 4. For example, it is also allowable to adopt a circular shape, an elliptic shape, a rectangular shape, and a polygonal shape. In FIG. 4, the minute pores 121*a* are arranged substantially regularly. However, the form of arrangement of the minute pores in the mesh sheet member 121 is not limited, on condition that the minute pores are pierced so that the inflowing injection solution can outflow through the minute pores. The minute pores 121*a* may be formed in a somewhat protruding state in an emboss form with respect to the mesh sheet member 121. It is also allowable to adopt a micro needle shape as described in U.S. Pat. No. 6,503,231. In this case, the respective protrusions are formed to be directed to the skin. However, it should be noted that if the minute pores are formed complexly on the mesh sheet member 121, the resistance that acts on the injection solution is increased and it becomes difficult to perform any preferable injection.

FIG. 3 shows a state in which the masking member 12 is attached to the side of the main syringe body 2 by means of the engagement between the pawls 123 and the groove 131, and the syringe is brought into contact with the skin as the injection target. In this situation, the mesh sheet member 121 is attached to the attachment cap 122 so that the outer surface of the mesh sheet member 121 (i.e. surface on the side on which the skin exists) is flush with the outer surface of the attachment cap 122 (surface on the side on which the skin exists as well). Owing to the construction brought about as described above, when the user brings the syringe 1 into contact with the skin, a state in which the skin is brought into contact with the outer side of the minute pores 121*a* is given. Therefore, the flows of the injection solution, which are thinly divided by the minute pores 121*a* as described above, are subjected to the injection into the skin without being greatly disturbed thereafter. It is possible to realize the intended injection depth corresponding to the size of the minute pore 121*a*.

In the construction shown in FIG. 3, the thickness of the attachment cap 122 is different from the thickness of the mesh sheet member 121. Therefore, when the attachment cap 122 is arranged to be flush with the mesh sheet member 121 on the outer surface as described above, the gap Δ is created between the inner surface of the mesh sheet member 121 and the side of the main syringe body 2 (attachment cap 13 and holder 5). This results from the difference in height brought about by the difference in thickness between the attachment cap 122 and the mesh sheet member 121. When the gap Δ is formed as described above, there is a possibility that the injection solution discharged from the open end may be somewhat diffused. Further, the injection solution remains in the gap, and hence a part of the injection solution may be wasted. Therefore, the shape in the side of the main syringe body 2 (attachment cap 13 and holder 5) is contrived so that the gap Δ is eliminated as much as possible and the difference in height is absorbed (or the side of the main syringe body can abut complementally on the unevenness).

The syringe 1 described above adopts the fixing method of the snap-fit system based on the engagement between the pawls 123 and the groove 131 for the masking member 12 having the mesh sheet member 121. Therefore, the masking member 12 is detachable with respect to the main syringe body 2 in this construction. The nozzle 4 is produced by means of the injection molding of resin. Therefore, it is difficult to process the size of the open end smaller than a certain dimension. However, when the mesh sheet member 121 is constructed detachably as in the present invention, the structure (i.e. the mesh sheet member), which finally determines the flow diameter of the injection solution to be injected into the skin, can be produced as a separate structure from the nozzle 4. When the structure is attached to the side of the main syringe body, the syringe 1 is formed. Therefore, it is possible to simplify the production of the syringe 1 which realizes the injection into the relatively shallow region. Further, when the structure is detachable, it is easy to realize the repetition of hygienic injections and an adjustment of the injection depth depending on the difference in the injection targets or in the injection target regions.

<Modified Embodiment>

Figure 5:
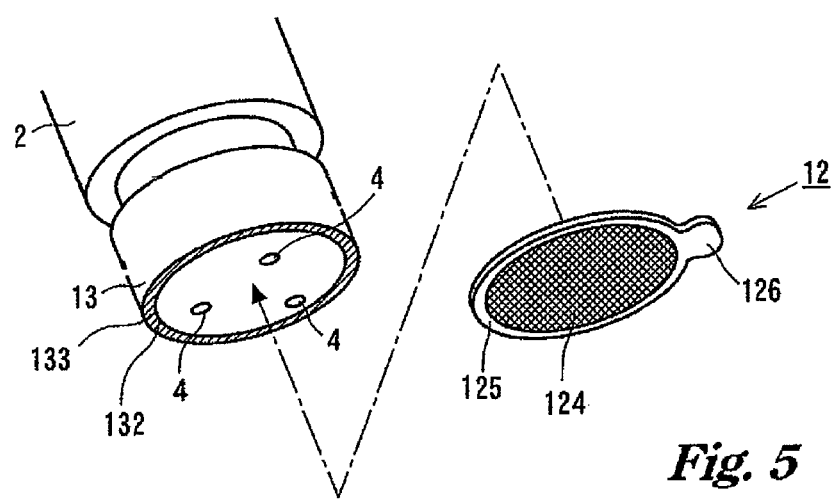
FIG. 5 shows a second drawing illustrating a situation in which a masking member is being mounted on the needleless syringe shown in FIG. 1A.
Figure 6:
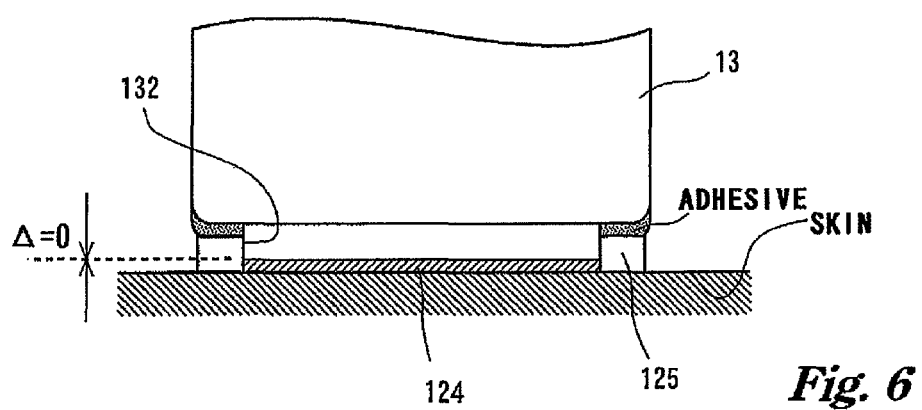
FIG. 6 shows a second sectional view illustrating a state in which the masking member is mounted on the needleless syringe shown in FIG. 1A.

A modified embodiment of the syringe 1 according to the present invention will be explained on the basis of FIGS. 5 and 6. In this modified embodiment, when a holder 5 is fixed by a holder cap 13, then the top of the holder 5 protrudes by a slight amount from the outer surface of the holder cap 13, and a protruding portion 132 is formed. As for the masking member, a mesh sheet member 124, which is constructed in the same manner as the foregoing embodiment, is attached so that the through-hole of an annular attachment frame 125 is closed. In this arrangement, as shown in FIG. 6, the outer surface of the mesh sheet member 124 is flush with the outer surface of the attachment frame 125. Further, the inner diameter of the through-hole of the attachment frame 125 is larger than the outer diameter of the protruding portion 132 by a slight amount.

As for the attachment of the masking member 12, with an adhesive being applied to the outer surface 133 of the holder cap 13 which adjoins the protruding portion 132, the masking member 12 is attached so that the through-hole of the attachment frame 125 is fitted to the protruding portion 132. When the attachment frame 125 is fitted along the protruding portion 132, the mesh sheet member 124 is brought into contact with the end surface of the protruding portion 132 (holder 5) as shown in FIG. 6. In this situation, such a state is given that the adhesive intervenes between the attachment frame 125 and the outer surface 133 of the holder cap 13, and the attachment of the masking member 12 is completed.

In the attachment form as described above, the inner surface of the mesh sheet member 124 is brought into contact with the end surface of the protruding portion 132. Therefore, the gap Δ between the mesh sheet member 124 and the open end of the nozzle 4 becomes substantially zero. Further, the attachment frame 125 is adhered to the outer surface 133 of the holder cap 13 owing to the thickness of the adhesive. Therefore, even when the distance between the attachment frame 125 and the outer surface 133 is more or less varied when the mesh sheet member 124 is brought into contact with the protruding portion 132, a secure attachment of the masking member 12 while allowing the gap Δ to become zero can be realized by adjusting the adhesive amount (thickness of adhesive) intervening therebetween. A grip portion 126, which is formed with a protruding part, is provided for the attachment frame 125. Therefore, the user can attach the masking member 12 while gripping the grip portion 126. Thus, it is possible to prevent the hand of the user from being dirtied by the overflowed adhesive. The masking member 12 is interposed tightly between the skin and the side of the main syringe body 2 (attachment cap 13 and holder 5) during the injection. It is enough for the adhesive to have the function to hold the masking member 12 on the side of the main syringe body 2 substantially during the period until the injection is performed. Thus the ability of the adhesive does not need to be so high. Therefore, it is also allowable to use a viscid layer such as double-sided tape or the like. When the masking member 12 is detached from the side of the main syringe body, it is preferable that the masking member 12 is detached with the adhesive or the viscid layer still adhered to the masking member 12.

When the injection of the injection solution is completed with the masking member 12 constructed as described above, then the masking member 12 is detached, and the remaining adhesive is removed. After that, a new masking member 12 may be attached. As for the masking member 12, the mesh sheet member 124 may be also fixed to the attachment frame 125 by an adhesive. In this case, it is preferable that the adhesive strength of the adhesive for attaching the masking member 12 is lower than the adhesive strength of the adhesive for fixing the mesh sheet member 124 so that the mesh sheet member 124 does not remain on the side of the main syringe body due to the adhesive for attaching the masking member 12 when the masking member 12 is detached after the injection.

<Second Modified Embodiment>

Figure 7A:
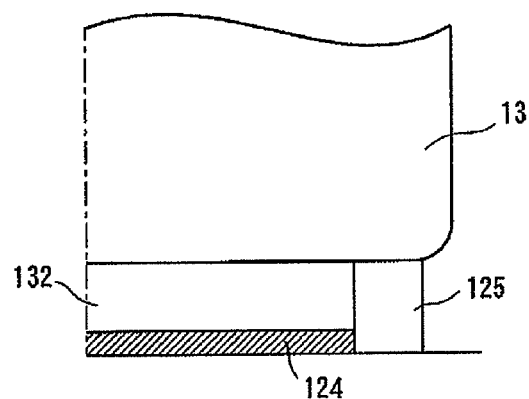
FIG. 7A shows a sectional view illustrating an installed state of a masking member in the needleless syringe according to the present invention.

Next, a modified embodiment of the syringe 1 according to the present invention will be explained on the basis of FIGS. 7A and 7B. In this modified embodiment, a protruding portion 132 of a holder 5 is formed, and a masking member 12 is constructed by a mesh sheet member 124 and an attachment frame 125 in the same manner as in the foregoing modified embodiment. In this arrangement, as shown in FIG. 7A, the inner diameter of the through-hole of the attachment frame 125 substantially coincides with the outer diameter of the protruding portion 132. When the masking member 12 is attached, the attachment frame 125 is press-fitted into the protruding portion 132. Accordingly, the masking member 12 can be firmly fixed without using any adhesive. The thickness of the attachment frame 125 is decreased as compared with the height of the protruding portion 132, and thus the press-fit can be performed until the mesh sheet member 124 is brought into contact with the protruding portion 132. In this case, creating a gap between the mesh sheet member 124 and the protruding portion 132 can be avoided.

Figure 7B:
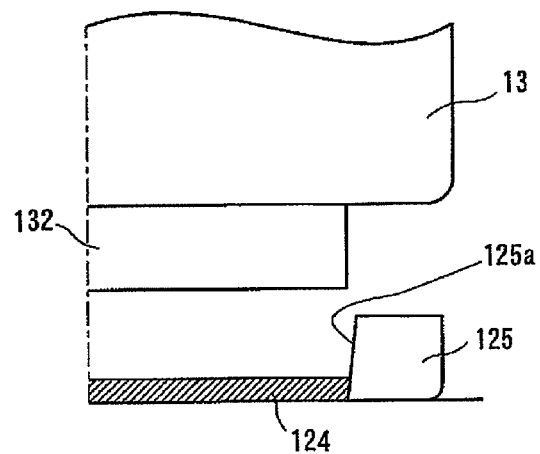
FIG. 7B shows a modified embodiment illustrating a sectional view to depict the mounted state of a masking member as shown in FIG. 7A.

As shown in FIG. 7B, an inner wall surface 125a of the through-hole of the attachment frame 125 may be formed to have a tapered shape. By doing so, the tapered portion serves as the guide upon press-fitting, making the press-fitting of the attachment frame 125 easy. In FIG. 7B, the inner wall surface 125a of the through-hole of the attachment frame 125 is formed to have the tapered shape. However, the side of the protruding portion 132 may be formed to have a tapered shape instead.

EXAMPLE 1

Experimental conditions and experimental results will now be shown below regarding the injection experiment performed by using the syringe 1 according to the present invention. The following experimental conditions are set in order that the injection solution is injected into a skin layer of a rabbit as the injection target. However, the syringe of the present invention is not limited to the use for a rabbit.

(Regarding the Pressurizing Unit 9 of the Syringe 1)

Figure 8:
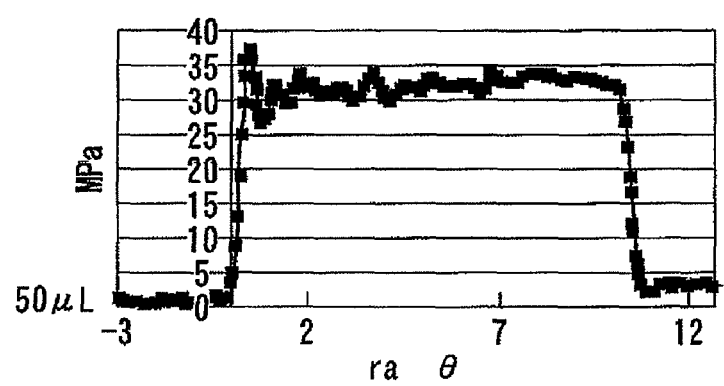
FIG. 8 shows the transition or change of the pressure applied to the injection solution in the needleless syringe according to the present invention.

The pressurizing unit 9 of the syringe 1 performs the pressurization on to the injection solution by utilizing the elastic force of the spring. FIG. 8 shows the transition of the pressurizing force with respect to the injection solution discharged from the nozzle 4 when the pressurization is performed by the pressurizing unit 9 for an amount of the injection solution of 50 μl. Specifically, the pressure transition is measured by a load cell arranged downstream from the nozzle 4. As also understood from the pressure transition, the pressurizing force temporarily exhibits the peak value at the initial stage of the pressurization for the syringe 1. However, after that, there is a tendency that the pressurizing force of approximately 30 to 35 MPa is maintained until the discharge of the injection solution is completed.

(Regarding the Injection Solution)

In order to understand the condition of the diffusion of the injection solution easily after the injection, a stained aqueous solution (methylene blue) was used.

<Experimental Conditions>

TABLE 1

|  | Experiment 1 | Experiment 2 | Comparative Example 1 |
|---|---|---|---|
| Injection solution amount | 50 μl | 50 μl | 50 μl |
| Pressurization transition | transition shown in FIG. 8 | transition shown in FIG. 8 | transition shown in FIG. 8 |
| Nozzle diameter | φ110 μm | φ110 μm | φ110 μm |
| Size of minute pore | □70 μm | □40 μm | no masking member |

<Experimental Results>

Figure 9A:
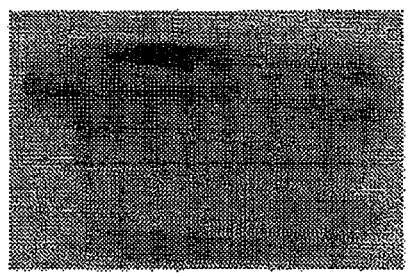
FIG. 9A shows a first drawing illustrating the injection result of a needleless syringe concerning Example 1 of the present invention.
Figure 9B:
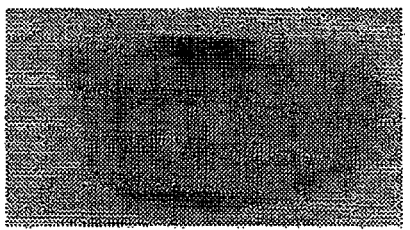
FIG. 9B shows a second drawing illustrating the injection result of the needleless syringe concerning Example 1 of the present invention.
Figure 9C:
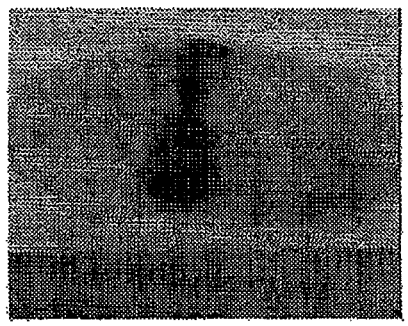
FIG. 9C shows a third drawing illustrating the injection result of the needleless syringe concerning Example 1 of the present invention.

Next, the experimental results in accordance with the foregoing experimental conditions are shown in FIGS. 9A to 9C. FIGS. 9A, 9B, and 9C show sectional views illustrating the skin structures of rabbits from the injection results in Experiment 1, Experiment 2 and Comparative Example 1 respectively. As for the skin structures of the rabbit, pieces of flesh with skin surfaces having approximately the same size were cryopreserved and were thawed at room temperature prior to the experiment. A predetermined amount of the injection solution was injected into each of the thawed pieces from the surface of the skin. After the injection, in order to make cutting easier, the pieces of flesh were once again frozen and then were cut. The conditions of the injected injection solutions were then observed. As evidenced by the experimental results, in the experimental result in Comparative Example 1 having no masking member 12, the injection solution, which is discharged from the open end of the nozzle 4, arrives at the deep layer region of the skin structure of the rabbit. However, in the experimental results of Experiment 1 and Experiment 2, the injection solutions remain at relatively shallow region (in the vicinity of the intradermal region) of the skin structure, and the injection solution does not arrive at the region deeper than the relatively shallow region. As shown in FIG. 8, the pressure, which is applied to the injection solution in the experiment described above, is approximately identical in each experimental condition. Taking this fact into consideration, it can be understood that when the syringe 1 is provided with the masking member 12 having the minute pores smaller than the nozzle diameter of the nozzle 4, it is possible to realize the injection into the relatively shallow region of the skin structure. As described above, this embodiment is illustrative of the case in which the injection is performed for a rabbit by way of example. However, the injection target is not limited, and the present invention is applicable to human as well. Further, injecting regions are not limited as well. The injection can be performed for respective regions by adjusting the minute pores 121a of the mesh sheet member 121, 124.

EXAMPLE 2

In relation to a second injection experiment performed by using the syringe 1 according to the present invention, experimental conditions and experimental results will now be shown below. The second experimental conditions are set in order that the injection solution is injected into a skin layer of a mouse as an injection target. However, the applicable range of the syringe of the present invention is not limited thereto.

(about Pressurizing Unit 9 of Syringe 1)

The same syringe 1 as that of Example 1 described above was used for the experiment. Therefore, the pressurizing ability brought about by the pressurizing unit 9 is as shown in FIG. 8.

(Regarding the Injection Solution)

As for the injection solution, a colored aqueous solution (methylene blue) was used in the same manner as in Example 1 described above.

<Experimental Conditions>

TABLE 2

|  | Experiment 3 | Comparative Example 2 |
|---|---|---|
| Injection solution amount | 50 μl | 50 μl |
| Pressurization transition | transition shown in FIG. 8 | transition shown in FIG. 8 |
| Nozzle diameter | φ110 μm | φ110 μm |
| Size of minute pore | □70 μm | no masking member |

<Experimental Results>

Figure 10A:
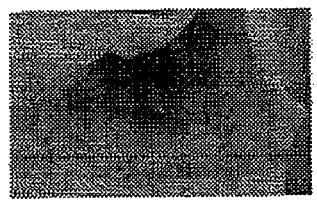
FIG. 10A shows a first drawing illustrating the injection result of a needleless syringe concerning Example 2 of the present invention.
Figure 10B:
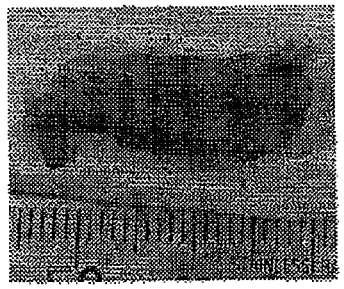
FIG. 10B shows a second drawing illustrating the injection result of the needleless syringe concerning Example 2 of the present invention.
Figure 10C:
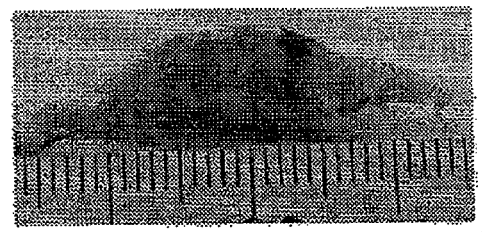
FIG. 10C shows a third drawing illustrating the injection result of the needleless syringe concerning Example 2 of the present invention.

Next, the experimental results in accordance with the foregoing experimental conditions are shown in FIGS. 10A to 10C. FIG. 10A relates to the injection result in Experiment 3 in which the skin was stripped off from the muscle layer after the injection, and the back side (inner side) of the skin was observed. FIG. 10B shows a sectional view illustrating the muscle layer that is left after its skin was stripped off. FIG. 10C shows a sectional view illustrating the skin structure of the mouse (in a state in which the skin is joined to the muscle layer) in the injection result in Comparative Example 2. As for the skin structures of the mouse, pieces of flesh with skin surfaces having approximately the same size were cryopreserved and were thawed at room temperature prior to the experiment. A predetermined amount of the injection solution was injected into each of the thawed pieces from the surface of the skin. After the injection, in order to make cutting easier, the pieces of flesh were once again frozen and then were cut. The conditions of the injected injection solutions were then observed. As evidenced by the experimental results, in the experimental result in Comparative Example 2 having no masking member 12, the injection solution, which is discharged from the open end of the nozzle 4, arrives at the deep layer region of the muscle layer of the skin structure of the mouse, as in the case of the rabbit of Example 1 described above. However, in the experimental result of Experiment 3, the injection solution is widely diffused at the relatively shallow region of the skin structure, i.e. the region in the vicinity of the lower layer of the skin, after the injection solution penetrates through the skin. As for the muscle layer, the injection solution merely adheres to the upper surface thereof and is not delivered deeply into the muscle layer. Therefore, even when a mouse is used, it can be understood that when the syringe 1 is provided with the masking member 12 having the minute pores smaller than the nozzle diameter of the nozzle 4, it is possible to realize the injection into the relatively shallow region of the skin structure.

<Other Embodiments>

According to the syringe 1 concerning the present invention, other than the case in which the injection solution is injected into the skin structure as described above, in the field of the regenerative medicine for human, for example, cultured cells or stem cells can be seeded to other cells or scaffold tissues as the injection target. For example, as described in JP2008-206477A, with the syringe 1, it is possible to inject those cells, such as endothelial cells, endothelial precursor cells, myeloid cells, preosteoblasts, cartilagenous cells, fibroblasts, skin cells, muscle cells, liver cells, kidney cells, intestinal tract cells, stem cells and all other cells considered in the field of the regenerative medicine, that are arbitrarily selected by those skilled in the art depending on the regions to which the cells are to be transplanted or the purpose of cell regeneration. More specifically, the solution containing the cells to be seeded (cell suspension) as described above is accommodated in the through-hole 14 by means of the sealing members 7, 8, and the pressurization is performed thereto. Accordingly, the predetermined cells are injected and transplanted to the region subjected to the transplantation.

Further, the syringe 1 according to the present invention can also be used to deliver DNA or the like to other cells, scaffold tissues or the like as described in JP2007-525192A. In this case, it is possible to suppress the influence exerted on the cells, scaffold tissues or the like when the syringe 1 according to the present invention is used, as compared with when the delivery is conducted by using a needle, and hence the use of the syringe 1 according to the present invention is more preferable.

Further, the syringe 1 according to the present invention is also preferably used when various genes, cancer suppressing cells, lipid envelops or the like are directly delivered to the target tissues and when any antigen gene is administered in order to enhance the immunity against the pathogen. Other than the above, the syringe 1 can be also used, for example, for the fields of the treatment of various diseases (fields described, for example, in JP2008-508881A and JP2010-503616A) and the field of the immune medicine (field described, for example, in JP2005-523679A). The field, in which the syringe 1 is usable, is not intentionally limited.

The pressurizing unit 9 of the syringe 1 shown in FIG. 1A performs the pressurization for the injection solution by utilizing the elastic force of the spring. However, in place thereof, a construction, in which the pressurization is performed for the injection solution by utilizing the pressure generated by the combustion of a propellant, can be also adopted as the pressurizing unit 9. A syringe 100 having the construction as described above is schematically shown in FIG. 11A.

Figure 11A:
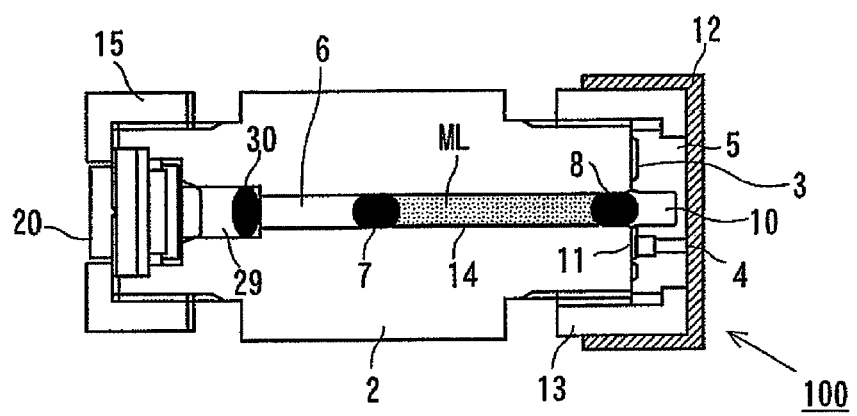
FIGS. 11A and 11B show a second drawing illustrating a schematic construction of a needleless syringe according to the present invention.
Figure 11B:
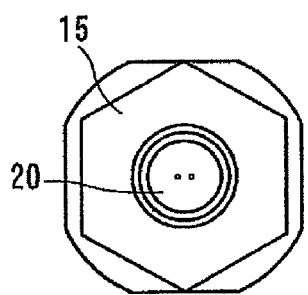

In this context, FIG. 11A shows a sectional view of the syringe 100, and FIG. 113 shows a side view illustrating the syringe 100 as viewed from a side of an initiator 20. Constitutive parts, which are substantially the same as those of the syringe 1 shown in FIG. 1A, are designated by the same reference numerals, any detailed explanation of which is omitted. In this construction, the syringe 100 has a main syringe body 2. A through-hole 14, which extends in the axial direction and which has a constant diameter in the axial direction, is provided at a central portion of the main syringe body 2. One end of the through-hole 14 is communicated with a combustion chamber 29 having a diameter larger than the diameter of the through-hole 14. The other end arrives at a side of a nozzle holder 5 formed with a nozzle 4. Further, the initiator 20 is arranged on the side opposite to the portion of the combustion chamber 29 communicated with the through-hole 14 so that its ignition unit is opposed to the communicated portion.

Figure 12:
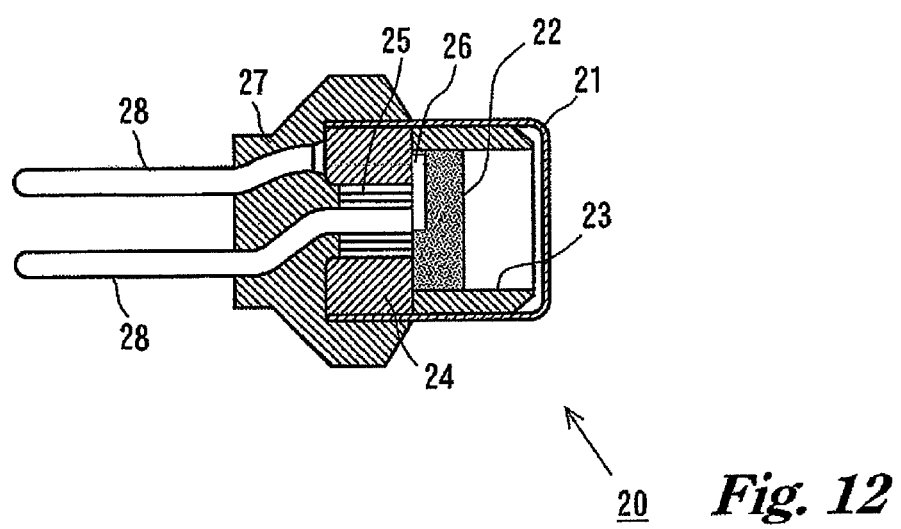
FIG. 12 shows a schematic construction of an initiator (ignition device) to be installed to the needleless syringe shown in FIG. 11A.

An example of the initiator 20 will now be explained on the basis of FIG. 12. The initiator 20 is an electric ignition device. A space for arranging an ignition charge 22 is defined in a cup 21 by the cup 21 having a surface covered with an insulating cover. A metal header 24 is arranged in the space, and a cylindrical charge holder 23 is provided on an upper surface thereof. The ignition charge 22 is held by the charge holder 23. A bridge wire 26, which electrically connects one conductive pin 28 and the metal header 24, is wired at the bottom portion of the ignition charge 22. Two conductive pins 28 are fixed to the metal header 24 with an insulator 25 intervening therebetween so that they are in a mutually insulated state. Further, an opening of the cup 21, from which the two conductive pins 28 supported by the insulator 25 extend, is protected by a resin 27 in a state in which the insulation performance is maintained to be satisfactory between the conductive pins 28.

In the initiator 20 constructed as described above, when the voltage is applied between the two conductive pins 28 by an external power source, then the current flows through the bridge wire 26, and the ignition charge 22 is combusted thereby. In this situation, the combustion product, which is produced by the combustion of the ignition charge 22, is discharged from the opening of the charge holder 23. Accordingly, in the present invention, the relative positional relationship of the initiator 20 with respect to the main syringe body 2 is designed so that the combustion product of the ignition charge 22, which is produced in the initiator 20, flows into the combustion chamber 29. Further, an initiator cap 15 is formed to have a brim-shaped cross section so that the initiator cap 15 is hooked by the outer surface of the initiator 20, and the initiator cap 15 is screw-fixed to the main syringe body 2. Accordingly, the initiator 20 is fixed to the main syringe body 2 by means of the initiator cap 15. Thus, the initiator 20 itself can be prevented from being disengaged from the main syringe body 2, which would be otherwise disengaged by the pressure brought about upon ignition in the initiator 20.

The ignition charge 22, which is used for the syringe 100, is preferably exemplified by a propellant containing zirconium and potassium perchlorate (ZPP), a propellant containing titanium hydride and potassium perchlorate (THPP), a propellant containing titanium and potassium perchlorate (TiPP), a propellant containing aluminum and potassium perchlorate (APP), a propellant containing aluminum and bismuth oxide (ABO), a propellant containing aluminum and molybdenum oxide (AMO), a propellant containing aluminum and copper oxide (ACO), and a propellant containing aluminum and iron oxide (AFO), or a propellant composed of a combination of a plurality of the foregoing propellants. The propellants as described above exhibit such a characteristic that the plasma having a high temperature and a high pressure is generated during the combustion immediately after the ignition, but when the temperature drops to normal and the combustion product is condensed, the generated pressure gets rapidly lowered as there will be no existing gas component. On condition that the adequate injection can be performed, it is also allowable to use any propellant other than the above as the ignition charge.

A gas producing agent 30 having a columnar shape, which is combusted by the combustion product produced by the combustion of the ignition charge 22 to produce the gas, is arranged in the combustion chamber 29. The gas producing agent 30 is exemplified, for example, by a single base smokeless propellant composed of 98% by mass of nitrocellulose, 0.8% by mass of diphenylamine, and 1.2% by mass of potassium sulfate by way of example. It is also possible to use various gas producing agents used for a gas generator for an airbag and a gas generator for a seat belt pretensioner. Unlike the ignition charge 22 described above, in the case of the gas producing agent 30, the predetermined gas, which is produced during the combustion thereof, contains the gas component even at the normal temperature. Therefore, the rate of decrease in the generated pressure is small as compared with the ignition charge 22 described above. Further, the combustion completion time upon combustion of the gas producing agent 30 is longer as compared with that of the ignition charge 22 described above. However, it is possible to change the combustion completion time of the gas producing agent 30 by adjusting the dimension, the size, and/or the shape, especially the surface shape of the gas producing agent 30 when the gas producing agent 30 is arranged in the combustion chamber 9. This is because the contacting state between the combustion product from the ignition charge 22 which flows into the combustion chamber 29, and gas producing agent 30 is considered to vary depending on the surface shape of the gas producing agent 30 or the relative positional relationship between the gas producing agent 30 and the ignition charge 22 owing to the arrangement of the gas producing agent 30 in the combustion chamber 29.

Next, the piston 6 made of metal is arranged in the through-hole 14 so that the piston 6 is slidable in the axial direction in the through-hole 14. One end thereof is exposed on the side of the combustion chamber 29, and the sealing member 7 is integrally attached to the other end. The injection solution ML, which is to be injected by the syringe 100, is accommodated in the space formed in the through-hole 14 between the sealing member 7 and the another sealing member 8.

In the syringe 100 constructed as described above, the combustion product or the predetermined gas is generated in the combustion chamber 29 by the ignition charge 22 of the initiator 20 and the gas producing agent 30 arranged in the combustion chamber 29 so that the pressure is applied to the injection solution ML accommodated in the through-hole 14 through the piston 6. As a result, the injection solution ML is extruded toward the forward end side of the syringe 100 together with the sealing members 7, 8. When the sealing member 8 is accommodated in the recess 10, then the injection solution ML passes through the flow passage 11 and the nozzle 4, and the injection solution ML is discharged to the injection target. The masking member 12 is also provided for the syringe 100 as described above, and thus the injection depth can be adjusted to be relatively shallow in accordance with the relative relationship between the size of the minute pores arranged therefor and the size of the open end of the nozzle 4.

REFERENCE SIGNS LIST

1: syringe, 2: main syringe body, 4: nozzle, 5: holder, 6: piston, 7,8: sealing member, 9: pressurizing unit, 10: recess, 11: flow passage, 12: masking member, 13: holder cap, 14: through-hole, 20: initiator, 22: ignition charge, 29: combustion chamber, 30: gas producing agent, 100: syringe, 121, 124: mesh sheet member, 122: attachment cap, 123: pawl, 125: attachment frame, 131: groove, 132: protruding portion.

The invention claimed Is:

1. A needleless syringe for injecting an injection substance into an injection target area of a living body without using an injection needle, the syringe comprising: an enclosing unit which encloses the injection substance, the enclosing unit having a flow passage area; a pressurizing unit comprising a spring or propellant which pressurizes the injection substance enclosed in the enclosing unit by exerting an elastic force or pressure generated by combustion of the propellant on a piston located within the enclosing unit; a nozzle in fluid communication with the enclosing unit, wherein the nozzle has a longitudinal flow passage having an open end, the open end having an area smaller than the flow passage area of the enclosing unit for the injection substance pressurized by the pressurizing unit to exit into the target injection area; and a minute pore unit which includes a planar member and an attachment member, the planar member having a plurality of minute pores, at least one minute pore of the plurality of minute pores having a flow passage area smaller than the area of the open end of the nozzle, the minute pore unit being arranged on an outer side of the open end so that the injection substance exiting the nozzle passes through the at least one minute pore before arriving at the injection target area, the attachment member being configured to attach the planar member to a distal side of the nozzle so that at least two of the plurality of minute pores of the planar member are aligned with the open end of the nozzle so as to cover the longitudinal flow passage of the nozzle when injecting the injection substance into the injection target area.

2. The needleless syringe according to claim 1, wherein the attachment member is fixed to the nozzle by being press-fitted into the nozzle.

3. The needleless syringe according to claim 1, wherein the at least two of the plurality of minute pores overlap the longitudinal flow passage of the nozzle.

4. The needleless syringe according to claim 1, wherein the at least two of the plurality of minute pores directly face the open end of the nozzle.

5. The needleless syringe according to claim 1, wherein the planar member is configured to be attached to and detached from the attachment member such that the planar member is exchangeable with another planar member.

6. The needleless syringe according to claim 5, wherein the attachment member is fixed to the nozzle by being press-fitted into the nozzle.

7. The needleless syringe according to claim 1, wherein when in a state in which the planar member is held by the attachment member, an outer surface of the planar member is flush with an outer surface of the attachment member to be brought into contact with the injection target area at the time of injection.

8. The needleless syringe according to claim 7, wherein the attachment member is fixed to the nozzle by being press-fitted into the nozzle.

9. The needleless syringe according to claim 7, wherein the planar member is configured to be attached to and detached from the attachment member such that the planar member is exchangeable with another planar member.

10. The needleless syringe according to claim 9, wherein the attachment member is fixed to the nozzle by being press-fitted into the nozzle.

11. The needleless syringe according to claim 7, wherein the planar member is configured to be attached to and detached from the attachment member such that the minute pore planar member is exchangeable with another minute pore planar member.

12. The needleless syringe according to claim 11, wherein the attachment member is fixed to the nozzle by being press-fitted into the nozzle.

13. An operating method for operating a needleless syringe for injecting an injection substance into an injection target area without using an injection needle, the needless syringe comprising an enclosing unit which encloses an injection substance, the enclosing unit having a flow passage area, and a pressurizing unit comprising a spring or propellant which pressurizes the injection substance enclosed in the enclosing unit by exerting an elastic force or pressure generated by combustion of the propellant on a piston located within the enclosing unit, the operating method comprising: pressurizing the injection substance enclosed in the enclosing unit by the pressurizing unit; guiding the injection substance pressurized by the pressurizing unit through a longitudinal flow passage and an open end of a nozzle to discharge the injection substance into the injection target area, the open end of the nozzle having an area smaller than the flow passage area of the enclosing unit; and guiding the injection substance through a minute pore unit, the minute pore unit including a planar member and an attachment member, the planar member having a plurality of minute pores, at least one minute pore of the plurality of minute pores having a flow passage area smaller than the area of the open end of the nozzle, the minute pore unit being arranged on an outer side of the open end of the nozzle so that the injection substance exiting the nozzle passes through the at least one minute pore before arriving at the injection target area, the attachment member being configured to attach the planar member to a distal side of the nozzle so that at least two of the plurality of minute pores of the planar member are aligned with the open end of the nozzle so as to cover the longitudinal flow passage of the nozzle when injecting the injection substance into the injection target area.

14. A needleless syringe for injecting an injection substance into an injection target area of a living body without using an injection needle, the syringe comprising: an enclosing unit enclosing the injection substance; a pressurizer comprising a spring or propellant configured to pressurize the injection substance enclosed in the enclosing unit by exerting an elastic force or pressure generated by combustion of the propellant on a piston located within the enclosing unit; a nozzle having a longitudinal flow passage through which the pressurized injection substance is configured to flow, the nozzle further having an open end from which the pressurized injection substance from the longitudinal flow passage is discharged towards the injection target area; and a masking member covering the open end of the nozzle and including a plurality of holes formed therein, wherein at least two of the plurality of holes of the masking member are aligned with the open end of the nozzle so as to cover the longitudinal flow passage of the nozzle when injecting the injection substance into the injection target area.

* * * * *